(12) United States Patent
Bennett et al.

(10) Patent No.: US 8,244,355 B2
(45) Date of Patent: Aug. 14, 2012

(54) METHOD AND APPARATUS TO PROVIDE DIAGNOSTIC INDEX AND THERAPY REGULATED BY SUBJECT'S AUTONOMIC NERVOUS SYSTEM

(75) Inventors: Tommy D. Bennett, Shoreview, MN (US); Edwin G. Duffin, North Oaks, MN (US); Barbro Kjellstrom, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1690 days.

(21) Appl. No.: 10/977,073

(22) Filed: Oct. 29, 2004

(65) Prior Publication Data

US 2006/0094967 A1    May 4, 2006

(51) Int. Cl.
*A61N 1/00* (2006.01)
(52) U.S. Cl. .......................... 607/18; 600/301; 600/513
(58) Field of Classification Search .................. 600/300, 600/301, 509, 513; 607/18
See application file for complete search history.

(56) References Cited

U.S. PATENT DOCUMENTS

| | | | |
|---|---|---|---|
| 5,042,497 A | 8/1991 | Shapland | |
| 5,203,326 A | 4/1993 | Collins | |
| 5,299,119 A | 3/1994 | Kraf et al. | |
| 5,330,513 A * | 7/1994 | Nichols et al. | 607/32 |
| 5,353,800 A | 10/1994 | Pohndorf et al. | |
| 5,419,338 A | 5/1995 | Sarma et al. | |
| 5,535,752 A | 7/1996 | Halperin et al. | |
| 5,564,434 A | 10/1996 | Halperin et al. | |
| 5,658,318 A | 8/1997 | Stroetmann et al. | |
| 5,919,221 A | 7/1999 | Miesel | |
| 5,921,940 A * | 7/1999 | Verrier et al. | 600/518 |
| 5,987,352 A | 11/1999 | Klein et al. | |
| 6,010,477 A | 1/2000 | Bays | |
| 6,077,277 A | 6/2000 | Mollenauer | |
| 6,152,885 A | 11/2000 | Taepke | |
| 6,155,267 A * | 12/2000 | Nelson | 128/899 |
| 6,171,252 B1 | 1/2001 | Roberts | |
| 6,221,024 B1 | 4/2001 | Miesel | |

(Continued)

FOREIGN PATENT DOCUMENTS

WO  01/97066 A  12/2001

OTHER PUBLICATIONS (PCT/US2005/039039) PCT Notification of Transmittal of the International Search Report and the Written Opinion of the International Searching Authority.

*Primary Examiner* — Scott M Getzow
(74) *Attorney, Agent, or Firm* — Reed A. Duthler; Stephen W. Bauer

(57) ABSTRACT

A system and method are provided for determining an index of autonomic nervous system (ANS) or sympathetic nervous system (SNS) activity for use in patient monitoring or therapy delivery control. An ANS or SNS index is calculated as a function of multiple monitored physiological variables that strongly correlate to changes in autonomic or sympathetic tone. These ANS-influenced variables are derived from selected hemodynamic and/or electrical signals and may include variables relating to any of: the maximum rate of pressure rise ($dP/dt_{max}$), the maximum rate of pressure decline ($dP/dt_{min}$), pulse pressure (PP), pre-ejection time interval (PEI) and/or systolic time interval (STI), heart rate (HR), heart rate variability (HRV), and baro-reflex gain. Changes in the ANS or SNS index may be used to automatically adjust a device delivered therapy.

14 Claims, 7 Drawing Sheets

U.S. PATENT DOCUMENTS

| | | |
|---|---|---|
| 6,234,973 B1 | 5/2001 | Meador et al. |
| 6,438,409 B1 | 8/2002 | Malik et al. |
| 6,571,122 B2 | 5/2003 | Schroeppel et al. |
| 6,572,558 B2 * | 6/2003 | Masakov et al. .............. 600/483 |
| 6,678,547 B2 | 1/2004 | Carlson et al. |
| 6,711,439 B1 | 3/2004 | Bradley et al. |
| 7,062,325 B1 * | 6/2006 | Krig et al. ....................... 607/14 |
| 2002/0128563 A1 | 9/2002 | Carlson et al. |
| 2003/0100924 A1 | 5/2003 | Foreman et al. |
| 2003/0191403 A1 | 10/2003 | Zhou et al. |
| 2003/0199937 A1 | 10/2003 | Carlson et al. |
| 2005/0165456 A1 * | 7/2005 | Mann et al. ..................... 607/30 |

* cited by examiner

METHOD AND APPARATUS TO PROVIDE DIAGNOSTIC INDEX AND THERAPY REGULATED BY SUBJECT'S AUTONOMIC NERVOUS SYSTEM

FIELD OF THE INVENTION

The present invention relates generally to implantable cardiac monitoring and therapy delivery systems and more particularly to a system and method for monitoring autonomic nervous system activity for use in patient monitoring and therapy control.

BACKGROUND OF THE INVENTION

Heart function is under the control of the autonomic nervous system (ANS) which includes the sympathetic nervous system (SNS) and the parasympathetic nervous system (PNS). Sympathetic nerve activity has a positive chronotropic effect on heart rate and contractility, which acts to increase stroke volume and cardiac output. Parasympathetic activity has a negative chronotropic effect on heart rate. The balance between SNS and PNS activity provides controlled regulation of heart function. Numerous factors provide feedback to the sympathetic and parasympathetic nervous systems, which can alter the SNS and PNS activity levels and, as a result, heart function. Under abnormal or disease states, disturbance of the coordination of autonomic nerve activity and balance between the SNS and PNS tone can lead to pathologic conditions such as arrhythmias and hemodynamic decompensation.

Therapies involving stimulation of the ANS for treating cardiac conditions have been proposed. Reference is made, for example, to U.S. Pat. Appl. 2003/0100924 to Foreman, et al., U.S. Pat. No. 5,203,326 to Collins, and U.S. Pat. No. 5,658,318 to Stroetmann, et al. Systems for monitoring physiological variables which vary in response to changes in autonomic tone have also been proposed. Such systems may further include delivering a cardiac therapy such as cardiac pacing in response to interpreted changes in autonomic tone. In U.S. Pat. No. 6,438,409 to Malik et al., a responsive descriptor for measuring autonomic tone is generally disclosed which involves measuring the cosine of the angle between each ventricular depolarization/repolarization vector pair. In U.S. Pat. No. 6,571,122 to Schroeppel et al., a method and apparatus for evaluating heart rate variability in order to forecast a cardiac event is generally disclosed. In U.S. Pat. No. 6,678,547 to Carlson et al., a cardiac rhythm management system that provides an indication of patient well-being based on the autonomic balance between the sympathetic and parasympathetic components of the ANS using time-domain processing of the frequency components of a heart rate interval signal is generally disclosed. U.S. Pat. Appl. No. 2003/0199937 to Carlson et al. generally discloses a cardiac rhythm management system that acquires atrial heart rate variability information as an indication of the autonomic balance between the sympathetic and parasympathetic components of the ANS. U.S. Pat. Appl. No. 2003/0191403 to Zhou et al. generally discloses an implantable medical device and method for assessing autonomic tone using a recurrence score calculated from changes in R-R interval, heart rate variability, patient activity and myocardial ischemia prior to and after an arrhythmia. The recurrence score may then be used to predict the early recurrence of an arrhythmia.

It is apparent that reliable assessment of autonomic tone would be useful in monitoring cardiac condition, predicting pathologic cardiac activity, and controlling cardiac therapies. However, many factors can influence autonomic tone, such as central venous pressure, central arterial pressure, body position, activity level, systemic vascular resistance, and blood volume. Assessment of ANS activity based on a single variable, which is likely to be influenced by other factors as well, may not be reliable at all times. Typically, clinical assessments of SNS or ANS tone are performed over a brief interval of time during which the patient's status is monitored to assure stable and reproducible stresses, which might independently alter the variable being used for the assessment. Such short-term assessments made during an office visit may not be representative of the patient's overall ANS status. A need remains, therefore, for a system and method for reliably assessing a patient's ANS activity for use in patient monitoring, diagnostics, and therapy management.

BRIEF SUMMARY OF THE INVENTION

The present invention provides a system and method for determining an index of ANS or SNS activity for use in patient monitoring or therapy delivery control. An ANS or SNS index is calculated as a function of multiple monitored physiological variables that strongly correlate to changes in autonomic or sympathetic tone. These variables may include any of: the maximum rate of pressure rise ($dP/dt_{max}$), the maximum rate of pressure decline ($dP/dt_{min}$), pulse pressure (PP), pre-ejection time interval (PEI) and/or systolic time interval (STI), heart rate (HR), heart rate variability (HRV), and baro-reflex gain.

The physiological variable measurements are derived from signals received from intra- or extra-cardiovascular sensors positioned for measuring cardiovascular hemodynamic and optionally electrical signals. SNS-influenced variables are derived from sensed signals and used in calculating an SNS index. Additional ANS-influenced variables may be determined and used in combination with the SNS index for calculating an ANS index. A comparative analysis of the SNS or ANS index values may be performed based upon which a patient and/or clinician notification may be generated. The results of a comparative analysis may additionally or alternatively be used in automatically controlling a device-delivered therapy.

DETAILED DESCRIPTION OF THE PREFERRED EMBODIMENTS

Figure 1:
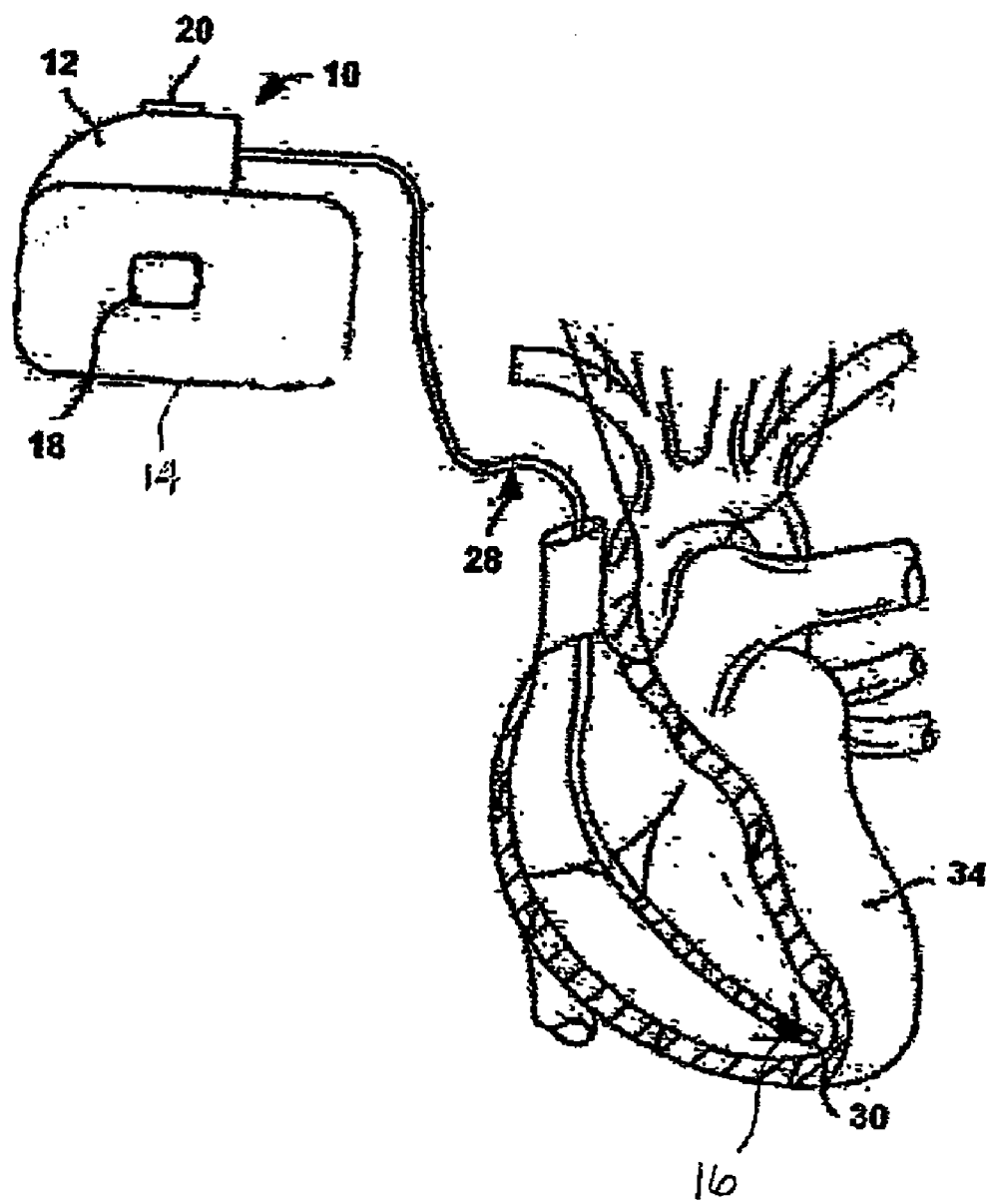
FIG. 1 is an illustration of an exemplary implantable medical device in association with a patient's heart.

FIG. 1 is an illustration of an exemplary implantable medical device (IMD) 10 in association with a patient's heart 34.

IMD 10 may be configured for both monitoring and delivering a therapy to heart 34. For example, IMD 10 may include a pulse generator to deliver electrical stimulation to heart 34 for use in cardiac pacing therapies, cardioversion or defibrillation. In accordance with the invention, IMD 10 obtains a signal indicative of dynamic mechanical activity of heart 34, and may optionally obtain an electrical signal indicative of electrical activity of the heart. Obtained signals are influenced by ANS activity and useful in deriving multiple ANS-influenced variables.

Using at least a mechanical signal of heart activity and optionally the electrical signal, IMD 10 determines an index of SNS activity and may further determine an index of ANS activity. The SNS and ANS index values may be stored by IMD 10 and made available to a clinician for diagnostic, prognostic or therapy management purposes. The SNS or ANS index may additionally be used in closed-loop algorithms implemented in IMD 10 for controlling therapy delivered to alleviate or prevent effects of disturbed SNS or ANS activity. The therapy may include drug delivery, electrical stimulation, or both.

IMD 10 is typically flat and thin to permit subcutaneous implantation within a human body, e.g., within upper thoracic regions or the lower abdominal region. IMD 10 includes a hermetically sealed housing 14 containing IMD circuitry and a connector block assembly 12 that receives the proximal ends of one or more medical leads for connection to circuitry enclosed within housing 14. In the example of FIG. 1, connector block assembly 12 receives a ventricular endocardial lead 28.

Ventricular endocardial lead 28 includes a pressure sensor assembly 16 to obtain a pressure signal and may alternatively or additionally include an accelerometer to obtain a heart acceleration signal. Alternative lead systems may be used including one or more leads equipped with pressure and/or accelerometer sensor assemblies for obtaining a signal influenced by ANS activity that are placed transvenously, epicardially, intrathoracically, endocardially, arterially or at other locations relative to the cardiovascular system. In other embodiments, a pressure signal can be obtained from outside a blood vessel, e.g., with the use of implantable blood vessel cuffs as described in U.S. Pat. Nos. 6,010,477 and 6,077,277 to Miesel et al.

Also, multiple accelerometers or pressure sensors can be used to achieve sensitivity at multiple hemodynamic locations. For instance, pressure sensors or accelerometers may be positioned for measuring hemodynamic changes in any heart chamber, the arterial system, the thoracic cavity, or the venous system. Multiple sensors may be desirable for enhanced reliability of the SNS or ANS index. Alternative types of sensors may be utilized to obtain signals that are equivalent or highly correlated to pressure or accelerometer signals for the purposes of deriving physiological variables influenced by the SNS or ANS. For example, impedance measurements which are useful for measuring changes in cardiac volume, a flow signal, or other hemodynamic signals may be substituted for or used in addition to pressure and/or accelerometer measures for obtaining ANS-influenced variable values.

The use of a pressure sensor will be generally described herein for purposes of illustration. A pressure sensor assembly 16 can be incorporated adjacent distal tip 30 of lead 28, and thereby deployed within heart 34. As will be described, housing 14 may enclose circuitry for use in analyzing the heart pressure signal produced by the pressure sensor to derive a number of variables influenced by SNS or ANS activity. Such variables are then used to calculate an SNS or ANS index.

In some embodiments, an EGM signal may be used in addition to a pressure signal to derive variable values influenced by SNS or ANS activity. To facilitate detection of electrical activity within heart 34, IMD 10 may include EGM sense electrodes 18 and 20. EGM sense electrodes 18 and 20 may be arranged substantially as described in U.S. Pat. No. 5,987,352, to Klein et al., which is incorporated herein in its entirety by reference. For example, electrodes 18 and 20 may form a pair of sense electrodes that are integrated with the exterior of housing 14 and connector block 12 of IMD 10. In alternative embodiments that include EGM sensing, sensing electrodes may be carried by a lead extending from IMD 10, such as lead 28 shown in FIG. 1, as is well known in the art. Ventricular endocardial lead 28 may be, for example, a bipolar, two wire lead equipped to sense electrical signals. Bipolar sensing electrode pairs may be carried on one or more leads extending from IMD 10. Alternatively, a unipolar sensing pair may include a lead-based sensing electrode and IMD housing 14.

As an advantage, a heart acceleration signal used for deriving SNS- or ANS-influenced variables can also be used to measure other events that may affect the same variables. For example, the heart acceleration signal may be monitored from 0 to 0.5 Hz for the patient's posture or orientation, from 1 to 5 Hz for the patient's activity, e.g., exercise, and from 5 to 100 Hz for the patient's heart acceleration. Thus, an accelerometer may serve multiple purposes in calculating an ANS or SNS index. For example, by analyzing the pertinent frequency bands, the accelerometer may be used to detect patient activity, patient orientation, and heart acceleration, which allows stratification of patient condition, e.g., rest or non-rest, at the time of ANS or SNS assessment.

Lead 28 may be configured for use as a diagnostic lead only for monitoring SNS and ANS activity and may additionally be configured as a therapeutic lead. For example, lead 28, in addition to a pressure sensor assembly 16, may carry sense electrodes, stimulation electrodes, or both. Distal tip 30 may include an electrode (not shown), as well as a number of stabilizing tines or other fixation members for securing distal tip 30 in cardiac tissue upon deployment. Lead 28 carries insulated electrical conductors coupled to any electrodes present and pressure sensor assembly 16.

Pressure sensor assembly 16 may be embodied as a relative pressure sensor, without requiring correction for changes in barometric pressure, for use in determining relative changes in the dynamic variables influenced by SNS and ANS activity. Alternatively, pressure sensor assembly 16 may be embodied as an absolute pressure sensor having correction for changes in barometric pressure, though measurement of absolute pressure is not necessary for practicing the present invention. Examples of implantable pressure sensors that may be used in conjunction with the present invention are generally disclosed in U.S. Pat. No. 5,535,752 to Halperin et al., U.S. Pat. No. 5,564,434 to Halperin et al., U.S. Pat. No. 6,234,973 to Meador et al., U.S. Pat. No. 5,919,221 to Miesel, U.S. Pat. No. 5,353,800 to Pohndorf et al., U.S. Pat. No. 6,152,885 to Taepke, U.S. Pat. No. 6,171,252 to Roberts, and U.S. Pat. No. 6,221,024 to Miesel, all of which patents are incorporated herein by reference in their entirety.

As indicated previously, an accelerometer may be substituted for or used in addition to pressure sensor assembly 16 for obtaining a SNS- or ANS-influenced physiological signal. An accelerometer may be embodied according to conventional accelerometer technology and may take the form of a piezoelectric, piezoresistive, capacitive, inductive, or magnetic sensor that produces a change in an electrical property with changes in accelerometric force within heart 34. The changes in the electrical property, e.g., resistance, capacitance, inductance, and the like, in turn produces changes in the electrical signal produced by accelerometer. An accelerometer assembly may be formed to have either one, two, or three detection axes and thereby be configured to detect wall motion extending in multiple directions as a result of the contractile force generated by heart 34.

In the example of FIG. 1, pressure sensor assembly 16 is mounted near the tip of distal end 30 of lead 28. Pressure sensor assembly 16, or an alternative sensor assembly could be mounted elsewhere along lead 28 provided the SNS- or ANS-influenced signal of interest is obtained with acceptable signal-to-noise ratio. Depending on the type of sensor used and the signal of interest, pressure sensor assembly 16 or an alternative sensor assembly may be positioned in an intracardiac location as shown in FIG. 1 or alternatively in an extra-cardiac location, intravascularly or extravascularly.

Figure 2:
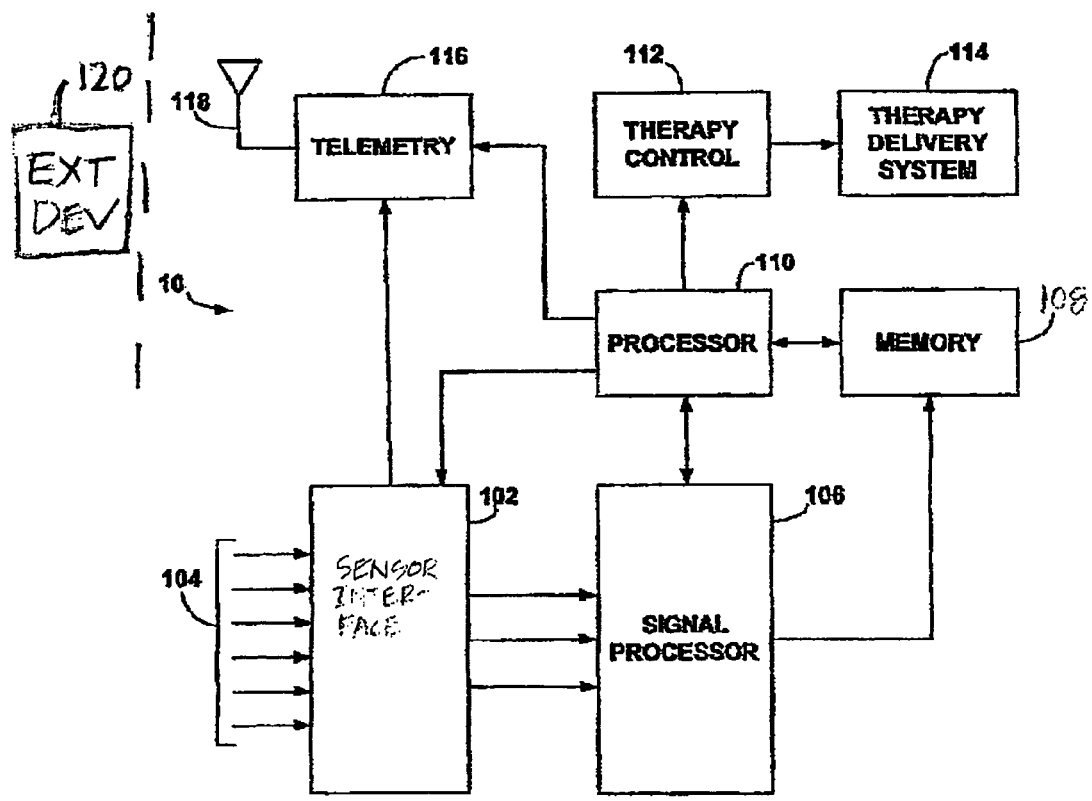
FIG. 2 is a simplified block diagram of a system for monitoring ANS or SNS activity.

FIG. 2 is a simplified block diagram of a medical device for monitoring ANS or SNS activity, such as IMD 10 shown in FIG. 1. System 100 includes a sensor interface 102 for receiving input 104 from one or more physiological sensors positioned for sensing an SNS- or ANS-influenced signal. Signal processor circuit 106 receives input from sensor interface 102 and processes the one or more sensed signals for deriving a number of SNS- and ANS-influenced variables.

A central processor 110 and associated memory 108 controls IMD 10 functions. Processor 110 may take the form of a microprocessor, microcontroller, digital signal processor (DSP) or other programmable logic device. Central processor 110 may receive derived variables from signal processor 108 or execute algorithms stored in memory 108 to derive SNS- and ANS-influenced variables from processed sensor signals received from signal processor 106. Central processor 110 calculates an SNS index, and may additionally calculate an ANS index, from the derived variables. The calculated indices may be stored in memory 108 such that they are available to a clinician for later review through uplink telemetry with an external device 120. External device 120 may be embodied as a programmer or monitor capable of bi-directional communication with IMD 10 via telemetry circuitry 116 and antenna 118. External device 120 may be used for transferring an interrogation command to IMD 10 to initiate uplink telemetry of stored SNS and ANS data. External programmers or monitors and associated telemetry systems for use with IMDs are well known in the art.

A therapy control circuit 112 and a therapy delivery system 114 may be included in IMD 10 for controlling and delivering a therapy, such as an electrical stimulation or medical therapy. Sensor interface 102 may be controlled by central processor 110 for selecting sensors, which may include EGM sensing electrode pairs, used in obtaining mechanical and electrical signal input 104 influenced by ANS activity.

Signal processor circuit 106 may include a number of sense amplifiers, sampling and comparator circuitry, integrators, peak detector circuitry and the like for analysis of the physiological signals received from interface 102 for deriving SNS- and ANS-influenced variable values. Alternatively, central processor 110 may digitally sample signals amplified by signal processor circuit 106 and perform a software-based analysis of the digital signals. Thus, signal processor circuit 106 may include an analog-to-digital converter that converts the analog signals received from sensor interface 102 into digital samples for analysis by central processor 110. Central processor 110 may provide the necessary control and clock signals for operation of signal processor circuit 106 and interface 102.

Memory 108 is provided for storage of digital samples produced by signal processor circuit 106 and intermediate data stored and retrieved by central processor 110. For example, signal processor circuit 106 may include a number of buffers that hold digital samples for storage in memory 108. Although not illustrated in FIG. 2 for simplicity, central processor 110, memory 112, and signal processor 106 may communicate via a common data and instruction bus, as is known in the art. The digital samples may be parameterized, in signal processor circuit 106 or central processor 110, to produce variable values for use in calculating an SNS and ANS index. Calculation of the SNS and ANS indices may occur within discrete circuitry provided by signal processor circuit 106, via code executed by central processor 110 or by a processor located in associated external device 120 after retrieving variable values from IMD 10. The code may include instructions carried by a computer-readable medium accessible by central processor 110, such as memory 108 or other fixed or removable media devices associated with an external device 120 communicatively coupled to the processor via telemetry device 116. External programmers or monitors having bi-directional communication with implantable medical devices for downlinking programming information and interrogation commands and uplinking data stored by the IMD are known in the art.

Signals provided by sensor interface 102 can be processed and parameterized to represent a variety of different values useful in calculating an SNS or ANS index. In one embodiment, a pressure signal may be processed to produce a heart rate, $dP/dt_{max}$, $dP/dt_{min}$, pulse pressure, and pre-ejection time interval (PEI). Each of these variables are influenced by SNS activity. Heart rate is under direct control of the ANS system where it is slowed by parasympathetic activity and increased by SNS activity. Heart rate can also be changed by blockade of the SNS, for example with the use of beta-receptor blockers. Ventricular $dP/dt_{max}$ and pulse pressure are under strong control of the SNS as increased SNS activity acts to increase myocardial contractility. Associated with changes in myocardial contractility, changes in myocardial relaxation may occur, reflected in the measurement of $dP/dt_{min}$. Increased SNS activity also increases conduction properties of the myocardium. Measures of PEI and/or systolic time interval (SI) are affected by the electrical and electromechanical coupling time of the myocardium. Increased SNS activity will cause a shortening of PEI and SI, when other influencing factors are constant. As other factors can influence each of these variables, inclusion of multiple SNS-influenced variables in the calculation of an SNS index improves the reliability of the index.

In addition to SNS-influenced variables for the calculation of an SNS index, ANS-influenced variables may be derived, which may be used in combination with the SNS index or any of the derived SNS-influenced variables, for calculating an ANS index. In one embodiment, a pressure signal may be used derive a heart rate variability (HRV) variable and a baro-reflex gain variable. Extensive study of heart rate variability (HRV) has documented that changes in HRV are strongly indicative of changes in the balance of the parasympathetic and sympathetic systems and thus reflective of the overall ANS state.

Baroreceptors, located in the systemic arterial and pulmonary arterial systems, provide the most important mechanism for short-term regulation of arterial pressure. The baroreceptor signals provide feedback to the SNS and PNS, which respond by altering activity levels controlling heart function (e.g., myocardial contractility and heart rate) and the peripheral blood vessels (vasoconstriction or relaxation).

The ANS response to baroreceptor feedback may be quantified by a "baro-reflex gain" variable. The baro-reflex gain may be estimated by measuring the heart rate response to cyclic changes in pressures known to contribute to the ANS baroreceptor reflex response. One cyclical pressure change that contributes to the baroreceptor reflex response is pressure change due to respiration. Cyclical changes in HR occur with the respiratory cycle. These cyclical HR changes will vary with variation in respiration pressures that occur with changing respiratory depth and rate. A respiration pressure signal may be obtained through low-pass filtering of a ventricular pressure signal. Thus, the baroreceptor reflex can be quantified as a "baro-reflex gain" measured by the magnitude of heart rate change relative to the magnitude of cyclical changes in respiration pressure. Mathematically, $$BRGAIN = \Delta HR/\Delta RESP\ PRESS \quad (1)$$

wherein BRGAIN is the "baro-reflex gain," $\Delta HR$ is the difference between the maximum and minimum heart rates that occur during one respiration cycle, and $\Delta RESP\ PRESS$ is the difference between the maximum and minimum respiration pressure during one respiration cycle, i.e., the pulse pressure of the respiration cycle. For processing purposes these values may be low-pass filtered and/or the results of multiple respiratory cycles may be averaged before calculating BRGAIN.

Based on an SNS or ANS index, central processor 110 may be programmed to effect therapeutic action. For example, central processor 110 may generate a therapy control signal that causes a therapy control circuit 112 to request delivery of therapy from a therapy delivery system 114. Therapy delivery system 114 may take the form of a drug delivery system or electrical stimulation system such as a cardiac pacing system which delivers arrhythmia prevention pacing therapies.

Central processor 110 also may control telemetry circuitry 116 to communicate an indication of a change in the SNS or ANS index to an external device 120 via antenna 118. The indication may be a wireless, radio frequency message that indicates a change for which clinical attention is recommended or may include the SNS and/or ANS index value. In addition, IMD 10 itself may have an audible alarm that notifies the patient when a change in SNS and/or ANS index is considered worthy of medical attention.

The external device 120 advises a clinician or other attendant of the SNS or ANS status, e.g., via a display or a visible or audible alarm. A history of the SNS and/or ANS indices may be stored in memory in the external device 120, or within the IMD, for review by a clinician. The components of IMD 10, with the exception of sensor leads 104, may be housed in a common housing as shown in FIG. 1. Alternatively, portions of the IMD 10 could be housed separately. For example, therapy delivery system 114 could be provided in a separate housing, particularly where the therapy delivery system includes drug delivery capabilities. In this case, therapy control circuit 112 may interact with therapy delivery system 114 via an electrical cable or wireless link. Furthermore, ANS-influenced signal acquisition may be performed by a combination of implantable and/or external devices capable of transferring signal data to a common device for SNS and ANS index computations.

Figure 3:
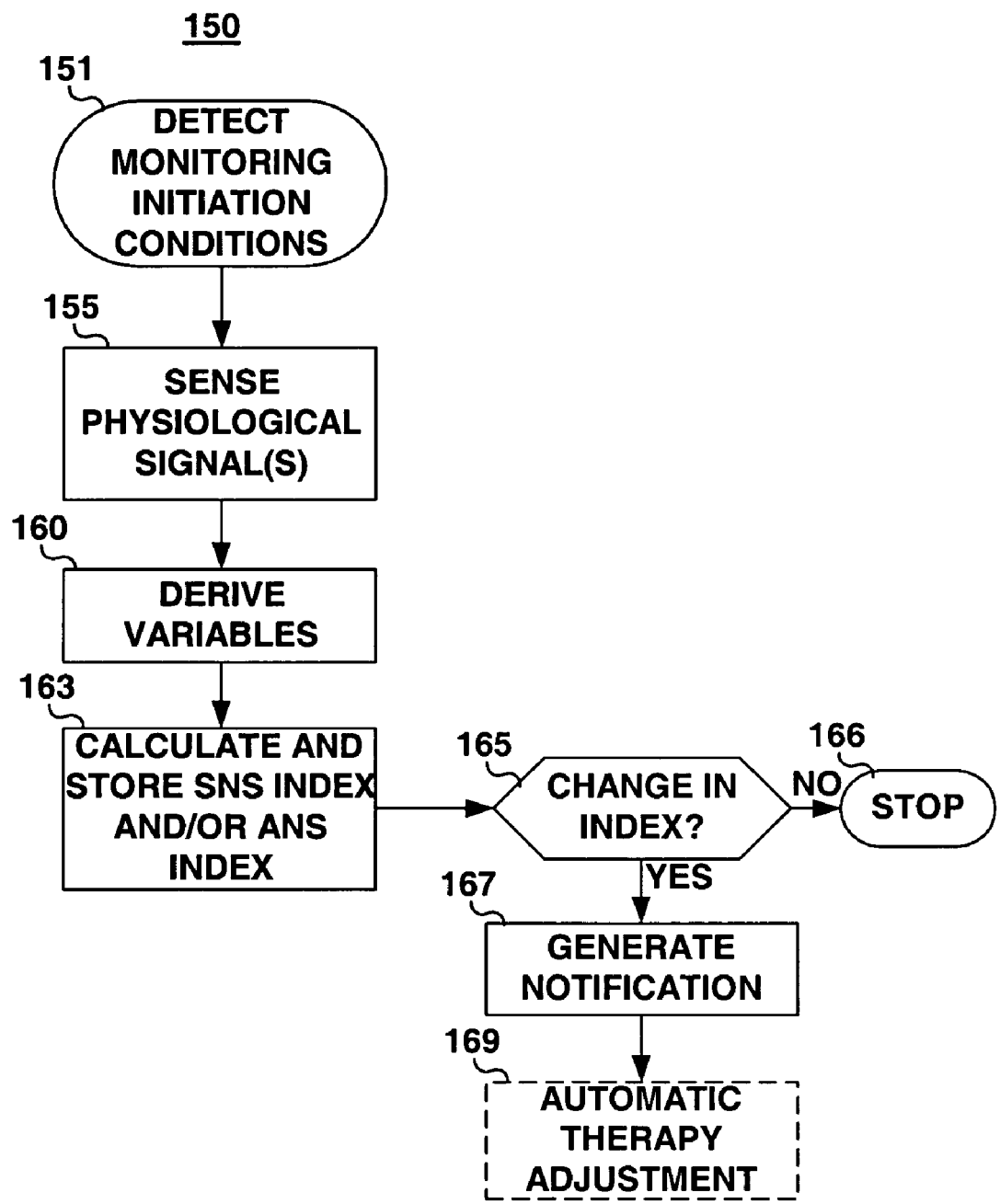
FIG. 3 is a flow chart providing a general overview of a method for monitoring SNS and/or ANS activity.

FIG. 3 is a flow chart providing a general overview of a method for monitoring SNS and/or ANS activity. At step 151, ANS or SNS monitoring is initiated when monitoring conditions are detected. Monitoring may occur at a scheduled time of day, upon manual initiation, or at times triggered by detecting conditions under which ANS or SNS monitoring is desired. Depending on the available device memory and power, monitoring of ANS-influenced variables may be performed continuously. ANS and/or SNS index values may be calculated or updated continuously or after specified intervals of data collection. Alternatively, under limited memory or power capacity, ANS-influenced variable data may be acquired at scheduled or triggered times for a specified interval of time after which an ANS and/or SNS index may be calculated.

One advantage of monitoring ANS or SNS activity in an implantable system is that variables influenced by the ANS can be monitored over relatively longer periods of time than during clinical assessments. Collection of ANS-influenced variables may be triggered to occur when specified temporal and/or patient-related conditions are satisfied. For example, ANS monitoring may be desired when one or more selected indicators verify that the patient is at rest. Such indicators may include time of day, heart rate, activity level, posture, respiration, or other metabolic indicators. SNS monitoring may be desired during periods of non-rest which may be indicated by time of day, patient activity level, heart rate, respiration, posture and/or other metabolic indicators. ANS and or SNS activity monitoring may be initiated at multiple levels of patient activity, e.g. rest, low activity, moderate activity, and high activity, each of which may be defined according to selected available indicator values that can be tailored specifically to individual patients.

In some embodiments, one or more selected ANS-influenced variables may be monitored continuously and used as an "index trigger." If a monitored variable or combination of variables cross a threshold or fall outside a predefined "normal" range, collection of other variables needed to calculate an ANS and/or SNS index may be triggered and the corresponding index calculated. Other factors relating to a patient's condition may be used for triggering ANS activity monitoring such as the occurrence of an arrhythmia or abnormal heart beats.

Once ANS or SNS activity monitoring is initiated at step 151, one or more physiological signals that are influenced by the ANS are sensed at step 155. Such signals may include an EGM or ECG signal; a pressure signal which may be a cardiac pressure signal such as right or left ventricular pressure or an arterial pressure such as aortic pressure or systemic or pulmonary arterial pressure; a wall motion or accelerometer signal; a blood flow signal such as aortic flow; a ventricular volume signal (typically measured by impedance sensing); or an acoustical signal containing heart sound information. ANS-influenced signals may be sensed and acquired by a single implantable device or by a combination of devices.

In some embodiments, multiple signals may be sensed to enable derivation of different ANS-influenced variables from each signal. For example, an EGM or ECG signal may be sensed for use in deriving heart rate and HRV in combination with a pressure signal for use in deriving $dP/dt_{max}$, $dP/dt_{min}$, and pulse pressure. An EGM or ECG signal may be used in combination with a pressure signal for determining a PEI or SI.

In other embodiments, multiple signals may be sensed to enable derivation of common ANS-influenced variables from each signal measured at different hemodynamic locations. For example, a pressure signal may be measured in each of the right ventricle, the left ventricle, and one or more arterial sites. A pulse pressure, $dP/dt_{max}$, and $dP/dt_{min}$ variable value may be determined from each of these measured sites and used to determine a combined variable value or redundant variable values that are used collectively or as subsets in an equation for calculating an SNS or ANS index. By providing multiple combined or redundant measures of a particular variable derived from multiple signal sources, the quantitative reliability of the SNS or ANS index may be enhanced.

At step 160, multiple ANS-influenced variables are derived from the sensed signal(s). Variable values determined at step 160 may be derived over any selected interval of time. For example variable values may be determined from a signal acquired over one or several cardiac cycles, minutes, hours, or even days. Thus, a derived variable value determined at step 160 may represent an average or other statistical aspect of a series of variable values, e.g. a PP variable may be an average or standard deviation of pulse pressure obtained over a predetermined time interval or number of cardiac cycles.

A derived variable value may alternatively represent a change in the status of a given variable. For example, a heart rate variable may be a change in the patient's heart rate determined over some specified time interval or number of cardiac cycles. A change in the status of a given variable may be measured as a change in a baseline value which may be a running average of a particular variable. For example a HR variable value may be the difference between a current heart rate, which may be an average determined over a predetermined interval of time, and a baseline heart rate determined as the average HR over a much longer interval of time. In a specific example, a HR variable value may be the difference between the average HR determined over a 24-hour period and the average HR determined over a one week period. A baseline value may alternatively be determined as a resting value derived from a sensed signal obtained during the night or when the patient is known to be at rest. Resting conditions may be confirmed with the use of an activity and/or posture sensor as is known in the art.

At step 163, an SNS index and/or ANS index are calculated from the derived variable values. Derived variable values may be combined in a simple linear function or in more complex mathematical functions represented generally as, for example:

$$\text{SNS Index} = f(\text{HR}, dP/dt_{max}, dP/dt_{min}, \text{PP}, \text{PEI}), \text{ and} \quad (2)$$

$$\text{ANS Index} = f(\text{SNS Index}, \text{HRV}, \text{BRGAIN}). \quad (3)$$

While specific variables are indicated here, including HR, $dP/dt_{max}$, $dP/dt_{min}$, PP, PEI, HRV, and BRGAIN, it is recognized that other ANS-influenced variables may be determined and included in a function for calculating an SNS or ANS Index. Variable values may be assigned weighting coefficients. Variables selected for use in calculating an SNS or ANS index and the assigned weighting coefficients may be tailored to individual patients.

In one embodiment, an SNS index may be calculated according to a simple, linear summation of weighted variable values:

$$\text{SNS Index} = a[f(\text{HR})] + b[f(dP/dt_{max})] + c[f(dP/dt_{min})] + d[f(\text{PP})] + e[f(\text{PEI})] \quad (4)$$

wherein a, b, c, d, and e represent weighting coefficients for each of the corresponding variable values each represented by f(X), which are determined as described above as a measure or function of selected SNS-influenced variables including, in this example, HR, $dP/dt_{max}$, $dP/dt_{min}$, PP and PEI.

Similarly, the ANS index may be calculated as a linear summation of weighted variable values:

$$\text{ANS Index} = k[f(\text{SNS index})] + m[f(\text{HRV})] + n[f(\text{BRGAIN})]$$

wherein k, m, and n are weighting coefficients assigned to corresponding variable values each represented by f(X), in this case SNS index, HRV, and BRGAIN. While the ANS Index is represented as a function of the SNS index, in addition to other selected variables, it is recognized that the ANS Index may be determined as a function of any combination of derived SNS-influenced variables instead of the SNS index. Some variables used in calculating an SNS index may be eliminated when calculating an ANS index or may be included but with a different weighting factor, exponential, or other functional expression than when used for calculating the SNS index.

As noted previously, multiple implantable devices may collect data for determining the multiple parameters used in calculating an ANS or SNS index. The multiple implanted devices may communicate information directly with each other or to a "master" implantable device having the capacity to integrate the data from the multiple sources and compute the ANS or SNS index. Alternatively, an associated external device may receive data from multiple internal devices through uplink telemetry. The ANS or SNS index may be computed and stored by the external device. In other embodiments, data may be transferred to a central database on a host server or clinical system for computation of the ANS or SNS index.

A comparative analysis of the computed index may be performed at decision step 165 to identify a clinically significant change in the computed index or an index value that falls outside a predefined "normal" range. The comparison made at step 165 may be simply a threshold comparison or may involve more complex comparisons, for example, wherein a variable threshold may be computed over a specified time window. Other comparative analysis methods known in the art may be used for detecting a change in SNS or ANS index. Examples of other methods include methods based on control chart theory and change point methods among others (e.g., see U.S. Pat. No. 6,155,267 to Nelson).

In the '267 patent to Nelson, an implantable medical device monitoring method and system monitors chronic data representative of at least one physiological parameter. The chronic data is monitored to detect changes in state of the at least one physiological parameter. Data associated with detected changes in state is stored within the implantable medical device. The detection of changes in state of the at least one physiological parameter is performed by establishing a baseline (e.g., a center reference line and upper and lower control limits), and then determining if the chronic data being monitored satisfies predetermined conditions (e.g., conditions based on the center reference line and the upper and lower control limits) indicative of a change in state of the at least one physiological parameter. The data stored in memory associated with the detected change in state of the at least one physiological parameter may, for example, include data representative of the center reference line and/or upper and lower control limits. Of course, yet other techniques can be utilized.

If the index is unchanged or within an acceptable range, method 150 is terminated at step 166. If a change in the SNS or ANS index is found that is considered to be clinically significant or an index value falls outside a predetermined "normal" range, a patient or clinician notification may be generated at step 167. The notification generated by an implanted device may be a warning flag stored with the SNS/ANS data, or may be a generated sound or vibration perceptible to the patient. If the notification is generated by an external device or centralized database system, a message may be displayed or transferred, for example by email, to alert the patient and/or clinician of a condition that may require medical attention. A clinician may make adjustments to cardiac therapies based on the ANS or SNS index change and associated data.

In some embodiments, an automatic adjustment to a device-delivered therapy may be made as indicated by optional step 169. The automatic adjustment may be made according to control algorithms implemented within the implanted device or an associated programmer or monitor through a local programming operation. Alternatively, automatic adjustment of a device delivered therapy be performed by a centralized programming instrument through a remote programming operation. For example, a change in an SNS index indicating elevated SNS activity may trigger an automatic adjustment of arrhythmia prevention therapies, arrhythmia detection and/or arrhythmia therapy sequences delivered by a cardiac stimulation device such that a more aggressive approach to preventing, detecting or treating arrhythmias is taken. In other embodiments, dosages of an anti-arrhythmic medical therapy delivered by an implantable drug pump may be adjusted.

Figure 4:
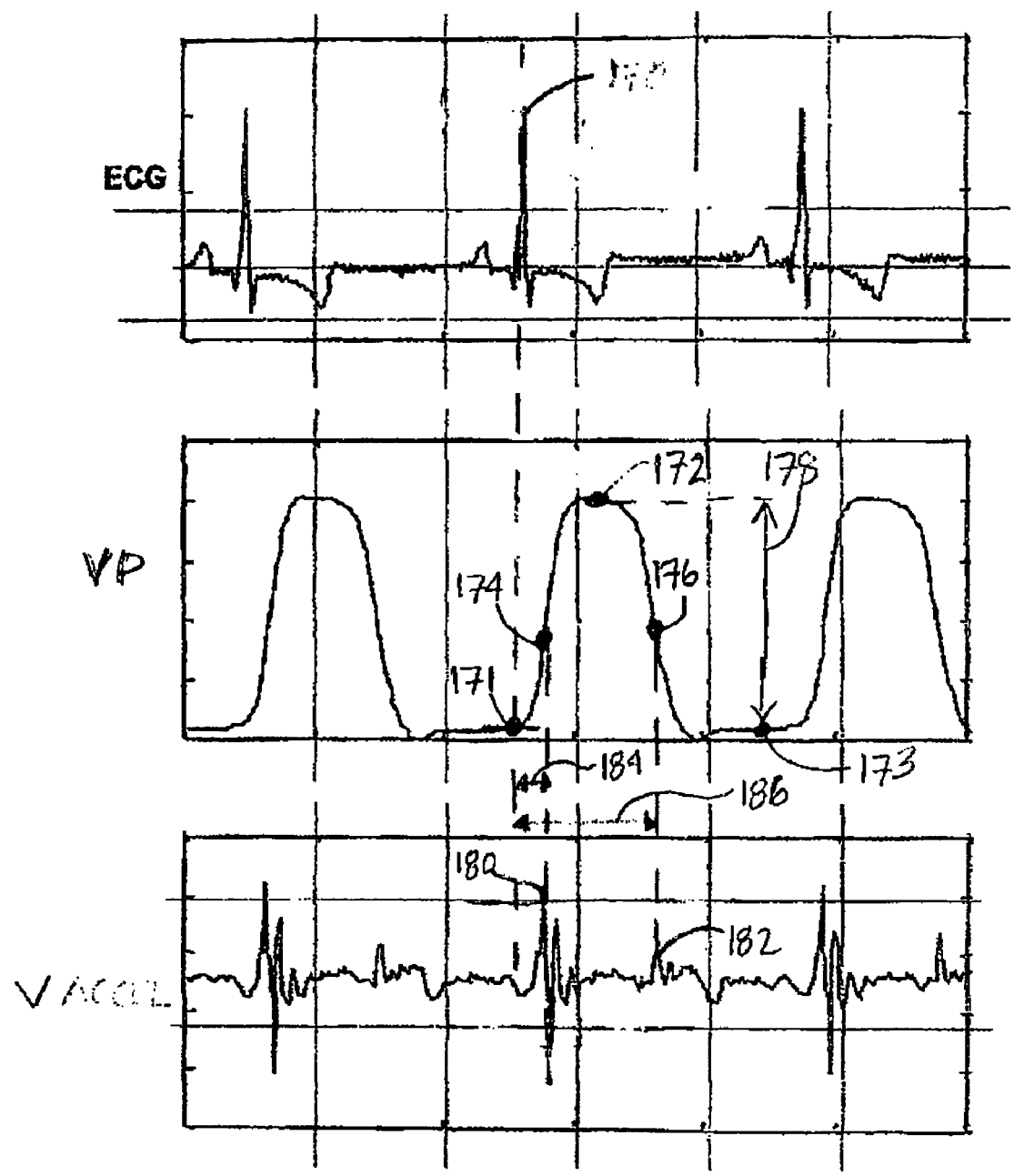
FIG. 4 is an illustration of ECG, ventricular pressure (VP), and ventricular acceleration (V ACCEL) recordings from which ANS-influenced variables may be derived.

FIG. 4 is an illustration of ECG, ventricular pressure (VP), and ventricular acceleration (V ACCEL) recordings. The onset of systole is hallmarked by the occurrence of an R-wave 170 on the ECG recording, which occurs as the ventricular mass is depolarized by a propagating action potential. As the ventricular cells contract, ventricular pressure rises. The maximum rate of rise, $dP/dt_{max}$ 174, coincides with the opening of the aortic and pulmonary valves and the onset of the rapid ejection phase. The onset of rapid ejection is marked by a peak ventricular acceleration signal 180, which coincides with the first heart sound on acoustical signals. The time interval between the R-wave 170 and the opening of the aortic and pulmonary valves is the pre-ejection time interval (PEI) 184. Ventricular pressure reaches a peak 172 and then begins to fall as ventricular contraction strength diminishes. At the point of $dP/dt_{min}$ 176, the aortic and pulmonary valves close, producing a second acceleration peak 182 observed on the accelerometer signal, marking the end of systole.

A number of ANS-influenced variables can be measured or estimated from the ventricular pressure signal alone. The pressure signal enables measurement of $dP/dt_{max}$ 174, $dP/dt_{min}$ 176, and pulse pressure (PP) 178 (as the difference between a minimum pressure 173 and a maximum pressure 172). Heart rate may be determined by measuring the time interval between two consecutive selected points on the pressure curve, e.g. from peak pressure 172 to the subsequently detected peak pressure or from $dP/dt_{max}$ 174 to the subsequently detected $dP/dt_{max}$. The PEI 184 may be estimated from a ventricular pressure signal as the interval between a threshold crossing 171 and $dP/dt_{max}$. For example one way of measuring PEI believed to be practiced by certain devices of Medtronic, Inc., the assignee of the present invention follows: PEI is measured as the time from detection of an R-wave maximum time-rate-of-change of (increasing) right ventricular pressure (i.e. $dP/dt_{max}$). Other devices have claimed a potentially related concept (also known as a "pre-ejection interval") measured as the time from the R-wave (or ventricular pace event) to peak intracardiac impedance (denoted as "dZ/dt"); that is, the maximum rate-of-chance of an intracardiac impedance signal measured within the heart. The latter form of "PEI" can be attributed to certain devices marketed by Guidant Corp., and possibly Precept Medical Products, Inc. too. Other ways to measure PEI are also known, albeit external versus the just-described internal methodologies. For example, the time interval from a detected R-wave to the "foot" (or beginning) of the arterial pressure rise can be utilized. This interval indicates that ejection of blood from the ventricle into the artery is starting and thus logically concludes that the "pre-ejection" interval has ended. A PEI has also been measured by Doppler echocardiology as the time interval from a detected R-wave to the moment the aortic (or pulmonic) valve opens.

Alternatively, a measure of the systolic interval (SI) 186 may be estimated as the time interval between a threshold crossing 171 and $dP/dt_{min}$ or as the interval between $dP/dt_{max}$ and $dP/dt_{min}$. Thus, using only a pressure signal, all the variables needed to calculate an SNS index according to the above equations may be obtained.

In other embodiments, an electrical (EGM or ECG signal) and/or the accelerometer signal may be used for deriving at least some of the ANS-influenced variables used in calculating an SNS index. EGM or ECG signals may be used for deriving heart rate as is well-known in the art. The PEI 184 may be measured as the interval between a detected R-wave 170 and $dP/dt_{max}$ 174 or the first accelerometer signal peak 180. SI 186 may be measured as the interval between a detected R-wave 170 and $dP/dt_{min}$ 176 or the second accelerometer signal peak 182.

In order to calculate an ANS index according to the above equations, a HRV parameter may be determined from cardiac cycle intervals measured between consecutive selected points on the ECG/EGM signal, pressure signal or accelerometer signal. More or less complex methods may be used to measure HRV. Methods for computing HRV in the time domain as well as in the frequency domain are known in the art. Frequency domain computation of HRV requires more complex computation methods such as Fourier transforms while time-domain computations use simpler computations such as standard deviation of the R-R interval. Simpler time-domain computations of HRV are more readily implemented in an IMD subject to power and memory constraints. Typically, HRV computation methods reject R-R intervals that are determined to be abnormal beats, e.g. ectopic beats. Methods for identifying abnormal beats such as premature ventricular contractions (PVCS) or premature atrial contractions (PACs) are known in the art and may be employed in accordance with existing HRV computational methods. Such methods may also be employed to eliminate abnormal beats from other ANS-influenced variable determinations.

Figure 5:
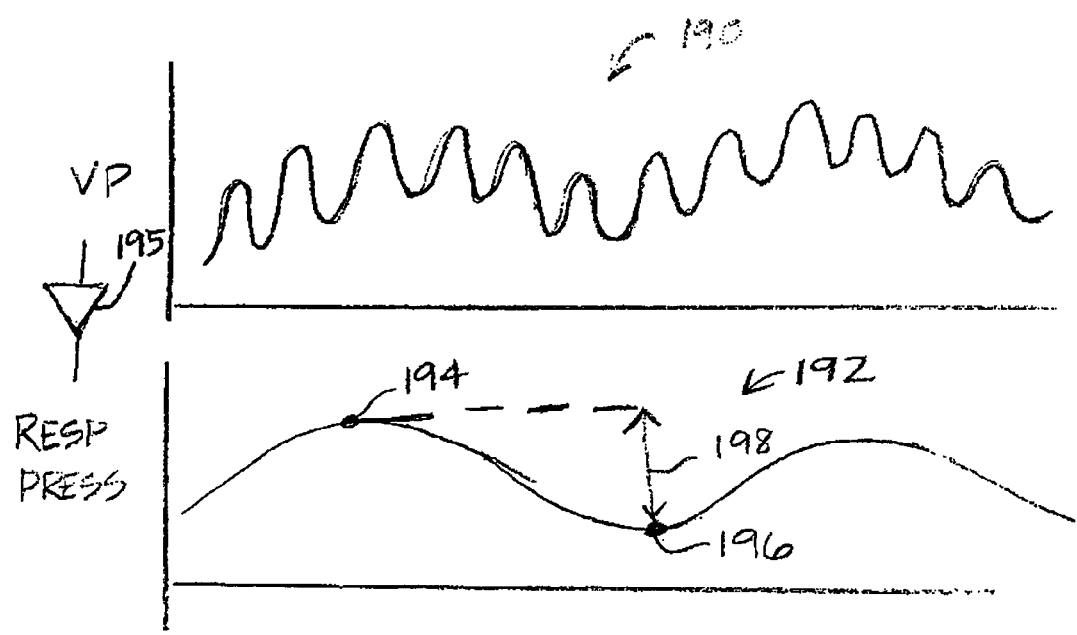
FIG. 5 is an illustration of a ventricular pressure signal and a respiration signal that may be used in determining a baro-reflex gain estimate for use in computing an ANS index.

FIG. 5 is an illustration of a ventricular pressure signal as it varies with respiration. By processing the ventricular pressure signal through a low pass filter 195, the low frequency component due to respiration may be obtained. The resulting respiration pressure signal 192 may be used to derive respiration depth and rate information. Respiration rate may be determined from the time interval between two consecutive selected points on the low-pass filtered ventricular pressure signal (respiration pressure signal 192), such as the time interval between maximum pressure 194 and the subsequently detected peak pressure. The respiration depth 198 may be estimated as the difference between maximum pressure 194 and minimum pressure 196. A baro-reflex gain parameter may be calculated from heart rate information derived from any of the pressure, EGM/ECG or accelerometer signals as described above and respiration rate and depth information derived from the respiration signal 192. A respiration signal may alternatively be obtained using a pressure transducer positioned within the thorax for measuring thoracic impedance as is known in the art.

Figure 6:
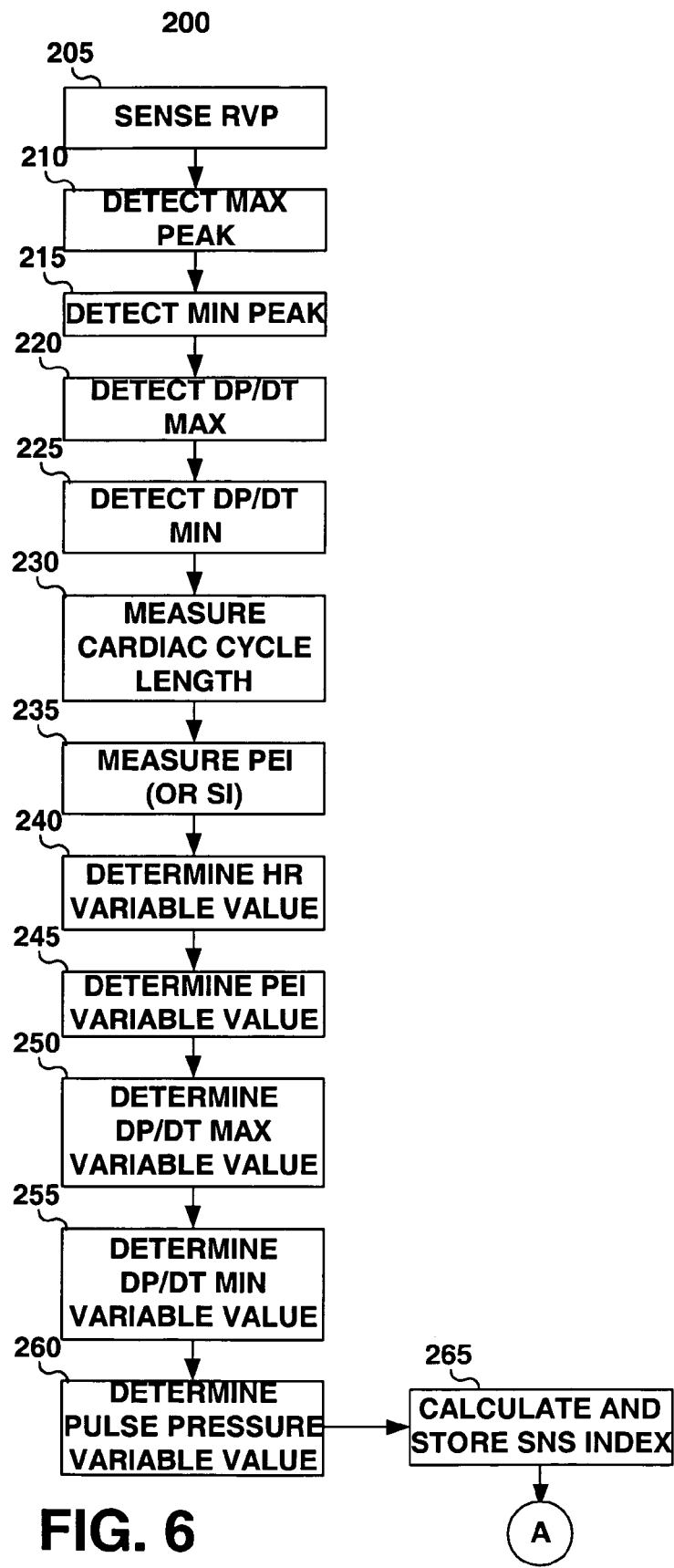
FIG. 6 is a flow chart providing greater detail of steps included in one method for monitoring SNS and/or ANS activity.

FIG. 6 is a flow chart providing greater detail of steps included in one method for monitoring SNS and/or ANS activity. The method 200 may be implemented in the system shown in FIGS. 1 and 2 wherein a right ventricular endocardial lead equipped with a pressure sensor assembly is used to obtain a right ventricular pressure (RVP) signal. At step 205, the RVP signal is sensed by the IMD. Using the methods as described above in conjunction with FIGS. 4 and 5 for analyzing a RVP signal, a number of ANS-influenced variables will be derived from detected points and time intervals measured on the RVP signal.

At step 210, a maximum pressure peak is detected, and at step 215 a minimum pressure peak is detected. At step 220 $dP/dt_{max}$ is detected, and at step 225 $dP/dt_{min}$ is detected. At step 230, the cardiac cycle length is measured between two selected points on the RVP signal. At step 235, the PEI or SI is measured between selected points on the RVP signal.

A HR variable value is computed at step 240 based on measured cardiac cycle lengths obtained at step 230. As described previously, the cardiac cycle length may be measured between any two consecutive selected points on the RVP signal, i.e. maximum pressure to maximum pressure. The HR variable value determined at step 240 may be the average HR determined over a predetermined time interval or number of cardiac cycles or a change in HR over a specified period of time or relative to a baseline HR, or other statistical or mathematical function of measured cardiac cycle lengths.

At step 245, a PEI variable value is determined. The PEI variable value may be determined as an average of a number of consecutive measured PEIs over a specified interval of time, a change in PEI over a specified period of time or relative to a baseline PEI, or other statistical or mathematical function of measured PEIs.

Likewise, a $dP/dt_{max}$ variable value and a $dP/dt_{min}$ variable value are determined at steps 250 and 255, respectively, as an average, change in or other statistical or mathematical function of the respective measured $dP/dt_{max}$ values and $dP/dt_{min}$ values. At step 260, the pulse pressure is determined as the difference between the maximum and minimum pressures detected at steps 210 and 215. A pulse pressure variable value is then determined as an average PP over a specified interval of time, a change in PP, or another statistical or mathematical function of the measured PPs.

At step 265, an SNS index is calculated as a function of the variable values determined at steps 240 through 260. As described previously, the SNS index may be a linear or a higher order or other non-linear function of the variable values, each of which may each be assigned a weighting coefficient.

Figure 7:
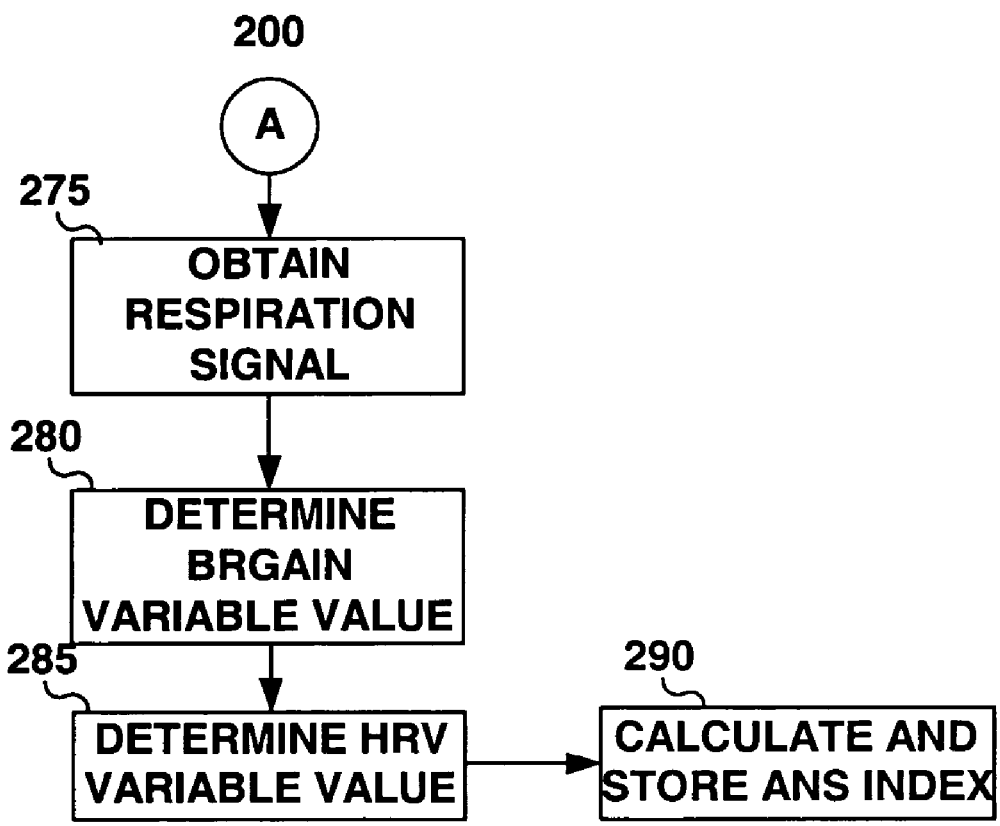
FIG. 7 is a continuation of the flow chart of FIG. 6 summarizing additional steps that may be included for monitoring ANS activity.

FIG. 7 is a continuation of the flow chart of FIG. 6 summarizing additional steps that may be included for monitoring ANS activity. Method 200 may optionally continue, from point A, to step 275 shown in FIG. 7 to derive ANS-influenced variables used in calculating an ANS index. At step 275, a respiration signal is obtained. A respiration signal may be obtained by low-pass filtering of the RVP signal obtained at step 205. At step 280, a baro-reflex gain variable value is determined based on heart rate change information derived from the RVP signal and respiration depth and rate information derived from the respiration signal. At step 285, a HRV variable value is determined, which maybe an average HRV, a change in HRV over a specified period of time or over a predetermined baseline, or another mathematical or statistical function of HRV derived from the RVP signal.

At step 290, the ANS index is calculated as a function of the SNS index, the HRV variable value, and the BRGAIN variable value. The ANS index may be a linear or a higher order or other non-linear function of these variables wherein each variable may also be assigned a weighting coefficient.

Thus, a system and method for monitoring a patient's ANS activity has been described. Detailed descriptions provided herein are intended to be illustrative of methods for practicing the present invention. The inventors have described apparatus and methods and consider the subject matter hereof to inherently include, as applicable, steps of the inventive methods to be susceptible of being stored as instructions in a computer readable medium (or a control signal-producing form). In addition, it is recognized that numerous variations of data acquisition and computational methods for determining an index of ANS or SNS may be conceived by one having skill in the art and the benefit of the teachings provided herein. The various embodiments presented herein should, therefore, be considered exemplary, not limiting, with regard to the following claims.

The invention claimed is:

1. A method for monitoring ANS activity via an implantable medical device (IMD), comprising:
    obtaining at least one physiological signal influenced by ANS activity via at least one sensor coupled to an IMD;
    deriving from the physiological signal a number of variables influenced by ANS activity; and
    computing an ANS index as a function of the derived variables; and
    wherein the at least one physiological signal is a pressure signal and the derived variables include any of dP/dt, pulse pressure, pre-ejection time interval, systolic time interval.

2. A method according to claim 1, wherein the variables further include baro-reflex gain and wherein the baro-reflex gain variable is derived from a measured change in heart rate occurring over a cyclic pressure change known to contribute to the baroreceptor reflex.

3. A method according to claim 2, wherein the cyclic pressure change is the cyclic pressure change in blood pressure caused by respiration.

4. A method according to claim 1, wherein the index of ANS activity is computed as a function of the derived variables each assigned a weighting coefficient wherein the weighting coefficient may be any real value.

5. A method according to claim 4, wherein the function of the derived variables is a linear function.

6. A method according to claim 4, wherein the function of the derived variables is a non-linear function.

7. A system for monitoring ANS activity, via an implantable medical device (IMD) comprising:
    an implantable medical device (IMD);
    a sensor that generates a signal influenced by ANS activity, coupled to said IMD;
    a processor that derives multiple variables influenced by ANS activity from the sensor signal, and
    means for computing an index of ANS activity from the derived variables; wherein
    the sensor comprises a mechanical sensor and the derived variables include at least one of: a blood pressure, a heart wall motion, a blood flow, a blood volume.

8. A system for monitoring ANS activity, via an implantable medical device (IMD) comprising:
    an implantable medical device (IMD);
    a sensor that generates a signal influenced by ANS activity, coupled to said IMD;
    a processor that derives multiple variables influenced by ANS activity from the sensor signal, and
means for computing an index of ANS activity from the derived variables; wherein
    the sensor is deployed on an deployable lead and comprises a pressure sensor; and
    wherein the processor derives the variables from the pressure sensor signal and the variables include at least one of: a dP/dt metric, a pulse pressure, a pre-ejection time interval, a systolic time interval.

9. A system according to claim 8, wherein the processor for deriving the variables further comprises means for processing the pressure sensor signal by any of:
means for identifying a maximum pressure;
means for identifying a minimum pressure;
means for identifying a maximum dP/dt;
means for identifying a minimum dP/dt.

10. A system according to claim 9, wherein the processor further includes means for deriving a baro-reflex gain variable further including means for measuring a change in heart rate occurring over a cyclic pressure change known to contribute to the baroreceptor reflex and means for measuring the cyclic pressure change.

11. A computer readable medium bearing instructions performed under computer processor control to provide a technical effect, said medium residing within an implantable medical device (IMD) and operatively coupled to internal circuitry disposed within said IMD, comprising:

instructions for obtaining at least one physiological signal influenced by ANS activity;
instructions for deriving from the physiological signal a number of variables influenced by ANS activity; and
instructions for computing an ANS index as a function of the derived variables; and
wherein the at least one physiological signal comprises a pressure signal and derived variables include at least one of: a dP/dt, a pulse pressure, a pre-ejection time interval, a systolic time interval.

12. A method according to claim 11, wherein the index of ANS activity is computed as a function of the derived variables each assigned a weighting coefficient wherein the weighting coefficient may be any real value.

13. A method according to claim 12, wherein the function of the derived variables is a linear function.

14. A method according to claim 12, wherein the function of the derived variables is a non-linear function.

* * * * *